United States Patent
Campagna

(10) Patent No.: US 9,733,319 B2
(45) Date of Patent: Aug. 15, 2017

(54) DEVICE, METHOD AND SYSTEM TO CONTROL AN IMAGING SYSTEM

(71) Applicant: Swen Campagna, Engelthal (DE)

(72) Inventor: Swen Campagna, Engelthal (DE)

(73) Assignee: Siemens Aktiengesellschaft, Munich (DE)

( * ) Notice: Subject to any disclaimer, the term of this patent is extended or adjusted under 35 U.S.C. 154(b) by 800 days.

(21) Appl. No.: 13/961,051

(22) Filed: Aug. 7, 2013

(65) Prior Publication Data
US 2014/0046617 A1    Feb. 13, 2014

(30) Foreign Application Priority Data
Aug. 7, 2012 (DE) .......... 10 2012 213 948

(51) Int. Cl.
G01D 1/00 (2006.01)
G01R 15/00 (2006.01)
G01R 33/28 (2006.01)
A61B 6/00 (2006.01)
A61B 6/03 (2006.01)

(52) U.S. Cl.
CPC ........... *G01R 33/28* (2013.01); *A61B 6/56* (2013.01); *A61B 6/03* (2013.01)

(58) Field of Classification Search
CPC .................................. G01R 33/28; A61B 6/56
USPC .............................. 702/122, 57, 62; 600/410
See application file for complete search history.

(56) References Cited

U.S. PATENT DOCUMENTS

2005/0169263 A1* 8/2005 Grottel ............ H04J 3/247
                                                            370/389
2008/0108891 A1* 5/2008 Campagna ........... A61B 5/055
                                                            600/410
2009/0251141 A1  10/2009 Baumgartl et al.

FOREIGN PATENT DOCUMENTS

EP        1 043 671        10/2000

OTHER PUBLICATIONS

Stang et al. "Medusa: A Scalable MR Console Using USB", IEEE Transactions on Medical Imaging, vol. 31, No. 2; pp. 370-379; (2012).
Stang et al., "A USB Approach to Scalable Design of MRI Systems", ISMRM 13th Sci. Meeting: Miami Beach (FL) (2005).
"TCP Receive Window" from German Wikipedia (2013).
"Message Broker" article from English Wikipedia (2013).

* cited by examiner

*Primary Examiner* — Gregory J Toatley
*Assistant Examiner* — Eman Alkafawi
(74) *Attorney, Agent, or Firm* — Schiff Hardin LLP

(57) ABSTRACT

A control device of an imaging system has a computer with communication interfaces for central control of the imaging system, and components each having a communication interface for local control of units of the imaging system. The communication interfaces of the components are respectively connected via a connection with an interface of the computer, and a transmitting component, among the components transfers data via the computer to a receiving component, among the components, for the exchange of information between the components.

4 Claims, 3 Drawing Sheets

DEVICE, METHOD AND SYSTEM TO CONTROL AN IMAGING SYSTEM

BACKGROUND OF THE INVENTION

Field of the Invention

The present invention is in the fields of medical engineering and information technology, and in particular concerns the control of imaging procedures and systems, for example diagnostic magnetic resonance (MR) procedures and MR systems, or other installations.

Description of the Prior Art

The conventional controller 10 (shown in FIG. 1) of a diagnostic MR system or MR scanner includes a computer 100, such as a measurement and control computer (measurement and reconstruction computer) or a measurement and control system (MARS) and n distributed components $200_i$-$200_n$, and is designated as a distributed controller. The components $200_i$-$200_n$ perform general communication tasks, control gradients of a gradient arrangement (gradient array), control a transmitter unit (TX unit) and process radio-frequency signals in the transmitter unit, or control a receiver unit (RX unit) and digitize radio-frequency (RF) reception signals in the receiver unit. The components $200_i$-$200_n$ can be arranged as close as possible to the respective, controlled system unit of the diagnostic MR system, for example in a control room, examination room or equipment room. Multiple components $200_1$-$200_n$ can be associated with one system unit or a component $200_1$-$200_n$ can be associated with multiple system units.

The computer 100 has n communication interfaces (ports) $110_1$-$110_n$, a processor 120 and memory 130. Each of n components $200_1$-$200_n$ has a respective communication interface $210_1$-$210_n$ that is connected via a computer connection $300_1$-$300_n$ with one of the interfaces $110_1$-$110_n$ of the computer 100 to transfer instructions and result data. Each of the components $200_i$-$200_n$ also has two communication interfaces $240_1$-$240_n$, $250_1$-$250_n$ that are respectively connected via a component connection $400_{1-2}$-$400_{n-1}$ with a corresponding interface $250_1$-$250_n$, $240_1$-$240_n$ of a component $200_1$-$200_n$ to transfer information, which component $200_1$-$200_n$ is (logically) arranged in parallel, such that the n components $200_1$-$200_n$ are connected with one another in the form of a ring (for example into a unidirectional or bidirectional MR control ring). Arbitrary components $200_1$-$200_n$ can thus directly exchange information among one another. For example, the components for gradient and RF transmission pulse control must exchange information in an extremely short and precisely reliable amount of time. The computer 100 generates instructions in an operating sequence provided thereto by processor 120 and a program for an MR measurement that is stored in the memory 130. These instructions are transferred to the various components $200_1$-$200_n$, and process result data that have been generated by the components $200_1$-$200_n$ and transferred to the computer 100.

In the prior art it is necessary to connect the n components $200_1$-$200_n$ among one another in order to enable them to exchange information among one another. For the example of n components $200_1$-$200_n$, the n components $200_1$-$200_n$ have 3n interfaces $210_1$-$210_n$, $240_1$-$240_n$, $250_1$-$250_n$, and the computer 100 has n interfaces $110_1$-$110_n$. Furthermore, the controller 10 for n components $200_1$-$200_n$ has n computer connections $300_1$-$300_n$ and n component connections $400_{1-2}$-$400_{n-1}$. The controller 10 overall thus has 4n interfaces $110_1$-$110_n$, $210_1$-$210_n$, $240_1$-$240_n$, $250_1$-$250_n$ and 2n connections $300_1$-$300_n$, $400_{1-2}$-$400_{n-1}$. In the transfer of information in the control ring, given n components $200_1$-$200_n$ one transmission (hop) from one component $200_1$-$200_n$ to a directly adjacent component $200_1$-$200_n$ is required in the best case, and in the worst case n/2 transmissions (given a bidirectional control ring) or n−1 transmissions (given a unidirectional control ring) are required from one component $200_1$-$200_n$ to a (logically) furthest remote component $200_1$-$200_n$. Since each component $200_1$-$200_n$ can generate a data rate $DR_1$, the maximum total data rate in the worst case amounts to $DR_{max}=Sum(DR_i)$, wherein each of the components $200_1$-$200_n$—and in particular their communication interfaces $240_1$-$240_n$, $250_1$-$250_n$—must be able to handle the maximum total data rate $DR_{max}$.

The large number of communication interfaces, the large number of connections, a high latency and a high required transfer speed to handle the data rate in the control ring are disadvantages of such a known controller 10.

SUMMARY OF THE INVENTION

An object of the present invention is to provide an improved controller.

In the following, the achievement of the object is described with regard to the disclosed device. Features, advantages and/or alternative embodiments that are mentioned herein apply analogously to the method, the system, and the computer-readable data storage medium in accordance with the invention. The corresponding functional features of the device are formed by corresponding, substantive computer-implemented modules, in particular microprocessor modules of the system. The device, the method and the system can also be integrated as embedded systems in the controller or the MR system.

In the following, the terminology used herein is explained in detail.

An imaging or image processing system is a system such as an electronic and/or information technology system that acquires, processes, evaluates and/or stores image information in the form of image data. For example, acoustic methods such as ultrasound (US), emission methods such as emission computer tomography (ECT) and positron emission tomography (PET), optical methods; radiological methods such as x-ray tomography and computed tomography (CT), magnetic resonance tomography (MR), or combinations of such modalities can be used to acquire image information. The image processing system can supply 2-dimensional (2D) or multidimensional—such as 3-dimensional (3D) or 4-dimensional (4D)—image data that are stored and/or processed in different formats. The image processing system can be used in diagnostics, for example in medical diagnostics.

The term "memory" emcompes a read-only memory (ROM) such as electrically erasable programmable read-only memory (EEPROM) or FlashEEPROM; read/write memory (random access memory, RAM); and disk storage, such as hard drives. The memory can be used to store a program (for example an operating system and/or an application program) and/or data (in particular image data, instruction data, configuration data, parameter data, protocol data and sequence data).

A processor (central processing unit, CPU) is, for example, a microprocessor or digital signal processor (DSP). The processor—which is controlled by the program, which can be divided up into a plurality of program modules—writes data into the memory, reads data from the memory and processes the data. The processor can also be executed as an (application) field programmable (logic) gate array (FPGA), for example.

One aspect of the invention concerns a control device of an imaging system, having a computer with communication interfaces for central control of the imaging system; and components with a respective communication interface for local control of units of the imaging system, wherein the communication interfaces of the components are respectively connected via a connection with an interface of the computer, and a transmitting component, among the aforementioned components, transmits data via the computer to a receiving component, among the aforementioned components to exchange information between the components With this aspect of the invention, the number of communication interfaces and the number of connections are reduced. For n components, the n components still have only n interfaces and the computer has n interfaces. Furthermore, the controller for n components still has only n computer connections. The controller thus has in total 2n interfaces, and n connections. Due to the savings of n interfaces and n connections, the costs and error tendency of the controller are significantly reduced since fewer devices are present that can be damaged or can fail.

Furthermore, the transfer of information between two of the components always requires only exactly two transfers, namely from the transmitting component (source component) to the computer and from the computer to the receiving component (sink component), and this is independent of the number n of components in the controller. The latency is thus consistent and independent of the number of components. Since each component that can generate a data rate $DR_i$ is connected with only the computer, each of the components (and in particular their communication interface) must be able to handle at the transmission side only the data rate $DR_i$, independently of the number of components in the controller. Each of the components that can receive data—in particular their communication interface—must be able to handle at the reception side only a data rate that is relevant to it. Since the type of information to be received is known, the components can be designed and implemented accordingly. The receiver-side data rate is normally lower or much lower than the maximum data rate $DR_{max}$. Although the computer must be able to handle the maximum data rate $DR_{max}$, a reduced latency and a reduced required transmission speed result. A greater scalability of the controller results from this, which is a central property of the system architecture of a controller. Moreover, a greater adaptation capability and improved updating capability result.

Another aspect of the invention concerns a control device, wherein the receiving component requests the information at the computer and the computer registers the request.

According this aspect of the invention, the computer (into which all information enter anyway) can transfer the information to the receiving component that requires the respective information without said receiving component needing to know the transmitting component.

An additional aspect of the invention concerns a control device wherein a transfer speed of the communication interface of a component among the aforementioned components is adapted to a data rate $DR_i$ of that component.

According to this aspect of the invention, the interface of the component is designed so that it can transfer the data rate $DR_i$ which the component generates. By adapting the interface to the data rate $DR_i$, an overdimensioning is avoided and the costs of the component are significantly reduced.

A further aspect of the invention concerns a control device wherein a transfer speed of the communication interface of the computer that is connected with the communication interface of the component is adapted to the data rate $DR_i$ of the component.

According to this aspect of the invention, the interface of the computer is designed so that it can transfer the data rate $DR_i$ which the component connected via said computer generates. By adapting the interface to the data rate $DR_i$, an overdimensioning is avoided and the costs of the computer are significantly reduced.

A further aspect of the invention concerns a control device wherein the computer centrally executes comprehensive tasks, for example control and monitoring of the information.

New functionalities, for example for control and monitoring, can be realized via this aspect.

A further aspect of the invention concerns a control device furthermore having a connection component $500_1$ with communication interfaces that is logically arranged between the computer and a group of components, wherein the communication interfaces of the components $200_2$-$200_4$ of the group are respectively connected via the connections with one of the interfaces of the connection component, and the communication interface of the connection component is connected via the connection $300_{n+1}$ with one of the interfaces of the computer.

The adaptability of the controller 2 to the individual case is increased via this aspect of the invention. Via the connection component the transfer of information between the components with this together with simultaneous unloading of the computer can be improved.

Using multiple, for example two, three, four or five, connection components, this aspect is adaptable to different topologies, for example hierarchies (such as recursive hierarchies), networks and layers. For example, a control device can furthermore have an additional connection component with communication interfaces that is logically arranged between the computer and the connection component wherein the communication interface of the connection component $500_1$ is connected via a connection with a communication interface of the additional connection component; and an additional communication interface of the additional connection component is connected via the connection with one of the interfaces of the computer. Alternatively, a control device can furthermore have an additional connection component with communication interfaces that is logically arranged in parallel with the connection component, wherein the communication interfaces of the components of an additional group are respectively connected via the connections with one of the interfaces of the additional connection component; and the communication interface of the additional connection component is connected via an additional connection with one of the interfaces of the computer.

A further aspect of the invention concerns a control device wherein the connections are executed in a wired, wireless or optical (for example by means of optical waveguides, OWG) manner.

Via this aspect of the invention, the possible transfer speeds are increased and the costs and error tendency are significantly reduced.

A further aspect of the invention concerns a control system of an imaging system, having a computer with communication interfaces for central control of the imaging system; and components with a respective communication interface for local control of units of the imaging system, wherein the communication interfaces of the components are respectively connected via a connection with an interface of the computer, and a transmitting component transfers data via the computer to a receiving component to exchange information between the components.

A further aspect of the invention concerns a computer-implemented method to control an imaging system having a computer with communication interfaces for central control of the imaging system and components, respectively with a communication interface for local control of units of the imaging system (the communication interfaces of the components are respectively connected via a connection with an interface of the computer), that includes the steps of transferring data from a transmitting component via the computer to a receiving component to exchange information between the components.

It is within the scope of the invention to execute the method steps in an order differing from that described above. Instead of relaying the information coming from the transmitting component directly to the receiving component, it is also alternatively possible (for example) to first conclude the reception of information from the transmitting component and only then send said information to the receiving component. In a further embodiment, the method steps can be interleaved with one another.

Moreover, it is possible for individual segments of the method described in the preceding to be designed as individual, salable units, and that the remaining sections of the method can be designed as other salable units. The method according to the invention can therefore be executed as a distributed system at different computer-based instances (for example client/server instances). For example, it is thus possible that a module for its part comprises different sub-modules that, for example, are implemented in part at the measurement system, in part at the reconstruction system and/or in part at other computer-based instances

DESCRIPTION OF THE PREFERRED EMBODIMENTS

Figure 1:
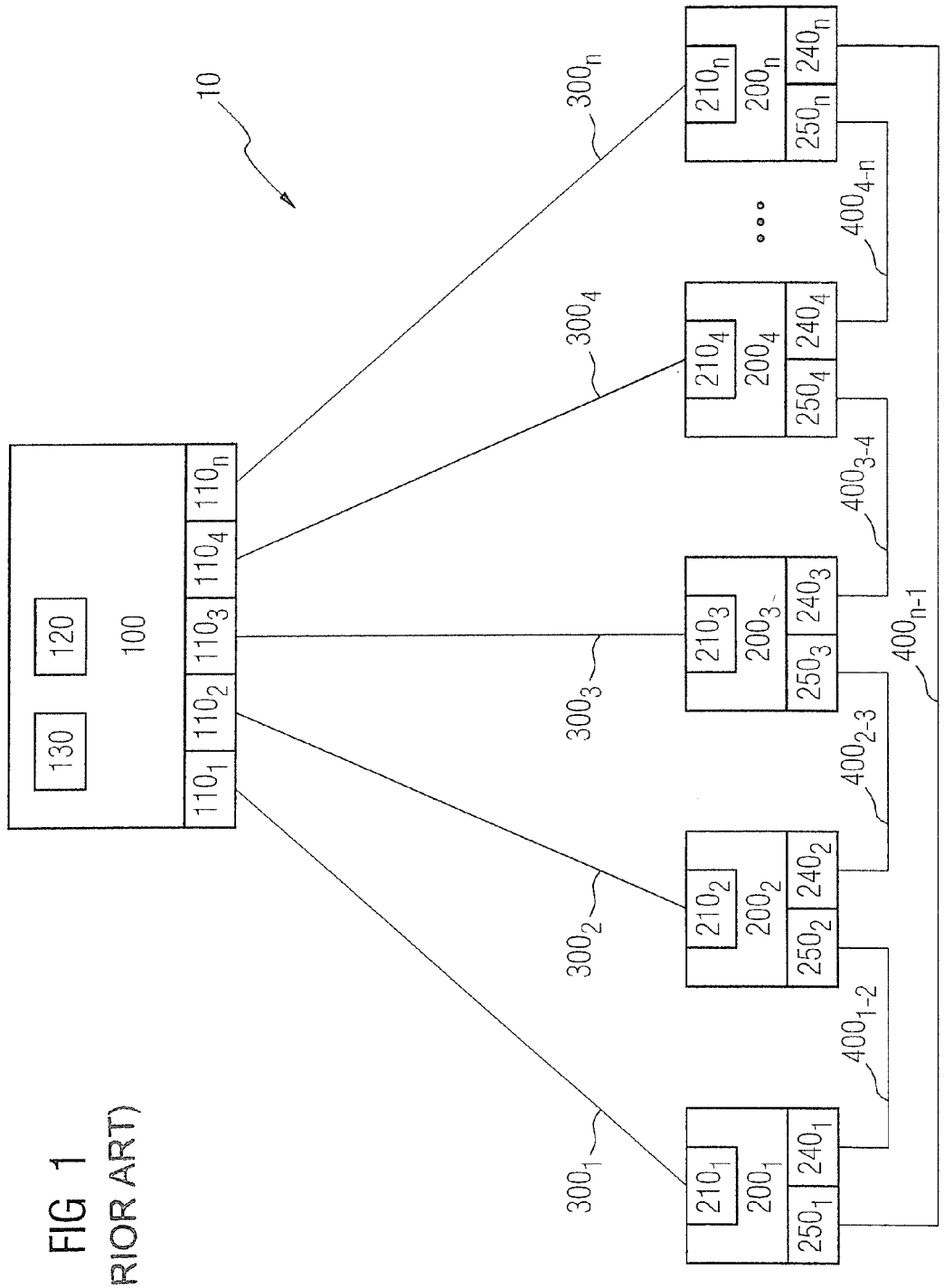
FIG. 1 schematically illustrates a known controller.
Figure 2:
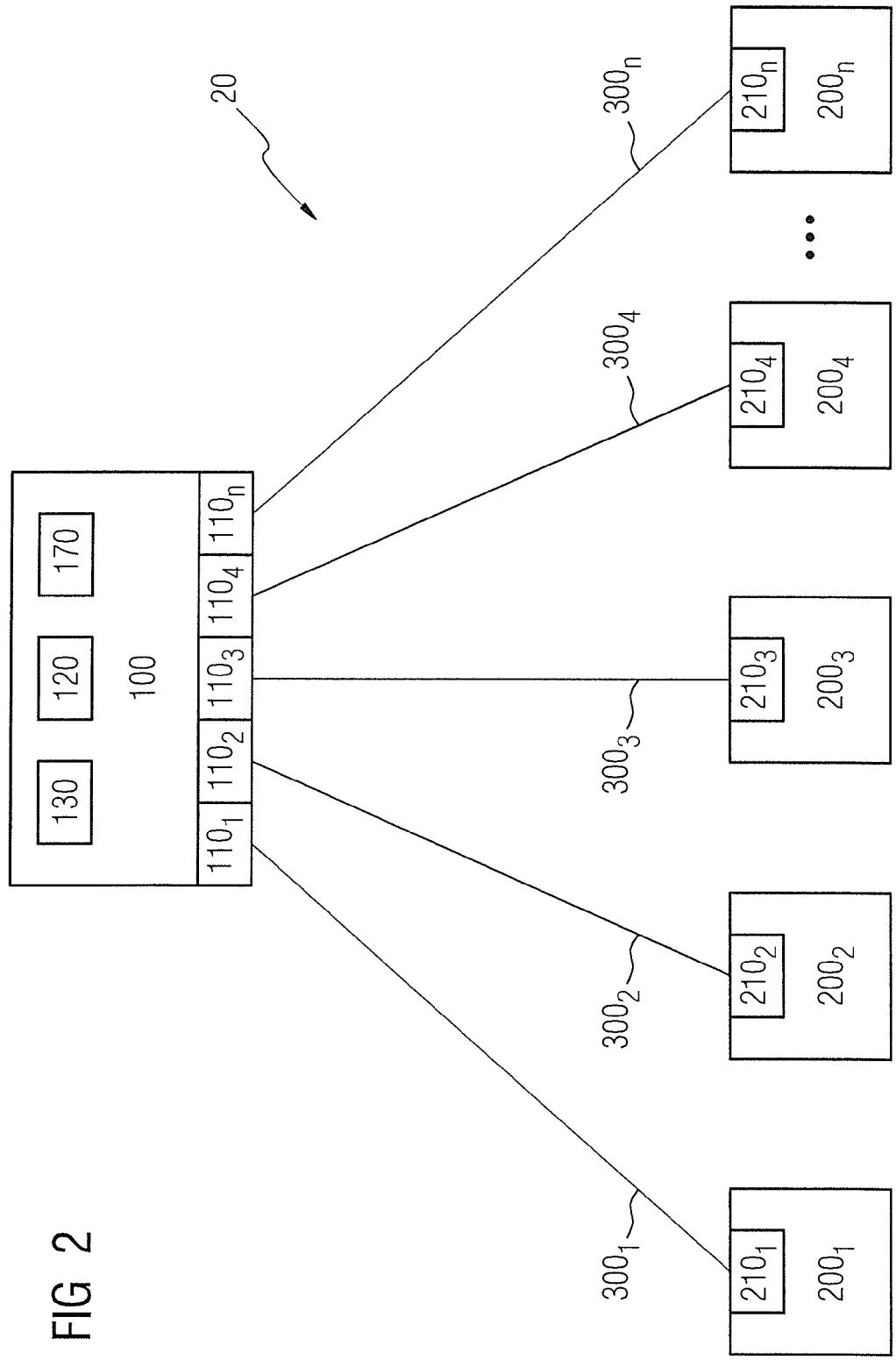
FIG. 2 schematically illustrates a controller according to a preferred embodiment of the invention.

FIG. 2 shows a schematic representation of a controller 20 according to a preferred embodiment of the invention. The controller 20 of an image processing system or imaging scanner has a computer 100, for example a measurement and control computer (measurement and reconstruction computer) or, respectively, a measurement and control system (MARS) and n distributed components $200_1$-$200_n$, and is designated as a distributed controller. The components $200_1$-$200_n$—for example for general communication tasks, to control gradients of a gradient arrangement (gradient array) to control a transmitter unit (TX unit) and to process radio-frequency signals in the transmitter unit or to control a receiver unit (RX unit) and to digitize radio-frequency (RF) reception signals in said receiver unit—can thus be arranged as close as possible to the respectively controlled unit of the image processing system, for example in a control room, examination room or equipment room. Multiple components $200_1$-$200_n$, can be associated with one unit, or one component among the components $200_1$-$200_n$ can be associated with multiple units.

The computer 100 has n communication interfaces (ports) $110_1$-$110_n$, a processor 120 and memory 130. Furthermore, the computer 100 can comprise a communication device 170. The communication device 170 can be executed in hardware (for example as a processor, DSP or FPGA) or in software (for example as a program module that is executed by the processor 120).

Each of the n components $200_1$-$200_n$ has a respective communication interface $210_1$-$210_n$ that is connected via a computer connection $300_1$-$300_n$ with one of the interfaces $110_1$-$110_n$ of the computer 100 for the transfer of instructions, information and result data. The computer connections $300_1$-$300_n$ can be executed in a wired, wireless or optical (for example by means of optical waveguides, OWG) manner.

The computer 100 generates instructions in an operating sequence by means of the processor 120 and a program (stored in the memory 130) for a measurement, which instructions are transferred to the various components $200_1$-$200_n$. The operating sequence also defines the processing of result data that have been generated by the components $200_1$-$200_n$ and transferred to the computer 100.

To exchange information between components $200_1$-$200_n$, a transmitting component $200_1$-$200_n$ transfers the information to the computer 100; and the computer 100 transfers the information to the receiving component $200_1$-$200_n$. For the transfer, the computer 100 can establish a direct connection (for example by means of the communication device 170) between the transmitting component $200_1$-$200_n$ and the receiving component $200_1$-$200_n$ or initially receive the information to be transferred from the transmitting component $200_1$-$200_n$, possibly process the information—for example store (buffer, for instance), associate, analyze, split up and/or merge it—and then send it to the receiving component $200_1$-$200_n$. The information can be transferred from a transmitting component $200_1$-$200_n$ to multiple (for example two, three, four or five) receiving components $200_1$-$200_n$. Furthermore, a receiving component $200_1$-$200_n$ can receive information from multiple (for example two, three, four or five) transmitting components $200_1$-$200_n$. The information can be transmitted as data (for example in data packets or data streams).

All information of the imaging system thus can be potentially available in the computer 100. A component $200_1$-$200_n$ that requires information from another component $200_1$-$200_n$ can request the information at the computer 100, which registers the request and transmits the information (after transfer from the other component $200_1$-$200_n$ to said computer 100) to the requesting component $200_1$-$200_n$. Since the computer 100 communicates the information, it is sufficient if the requesting component $200_1$-$200_n$ specifies the information; the requesting component $200_1$-$200_n$ neither needs to know nor specify the other component $200_1$-$200_n$.

Furthermore, the computer 100 can centrally execute comprehensive tasks, for example control and monitoring of the system and the information. The availability of specific information can be regulated (in particular limited), for example via a rights system.

A (maximum) transfer speed of the communication interface $210_1$-$210_n$ of the components $200_1$-$200_n$ can respectively be adapted to a required data rate $DR_i$ of each component $200_i$. Furthermore, the (maximum) transfer speed of the communication interfaces $110_1$-$110_n$ of the computer 100 can respectively be matched to the transfer speed of the corresponding connected communication interfaces $210_1$-$210_n$ of the components $200_1$-$200_n$.

According to a modification of the preferred embodiment of the invention, one or more interfaces $110_1$-$110_n$ of the computer 100 can be physically arranged in an interface unit of the computer 100 that can be spatially displaced from the computer 170. The interface unit can be connected with the computer 100 via an internal computer connection, for example a Peripheral Component Interconnect Express (PCIe or PCI-E) connection or extension. The interface unit can furthermore comprise the communication device 170.

Figure 3:
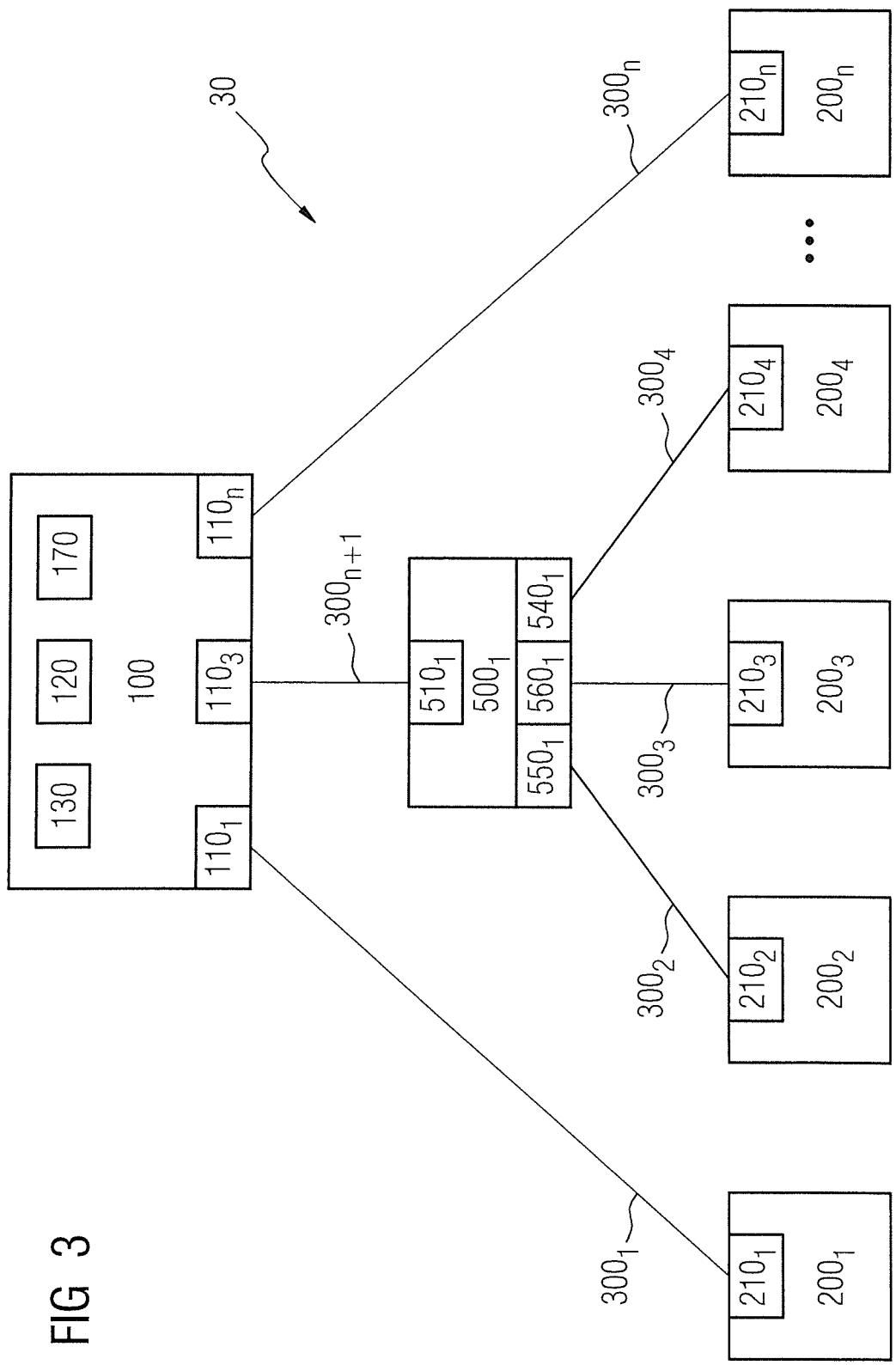
FIG. 3 schematically illustrates a controller according to a further embodiment of the invention.

FIG. 3 shows a schematic representation of a controller 30 according to a further embodiment of the invention. The controller 30 furthermore comprises a connection component $500_1$. The connection component $500_1$ comprises communication interfaces $510_1$, $540_1$, $550_1$ and $560_1$ and is (logically) arranged between the computer 100 and a group of components $200_2$-$200_4$. The components $200_2$-$200_4$ of the group are, for example, associated with a unit (such as a TX unit).

The components $200_2$-$200_4$ of the group are respectively connected via their communication interfaces $210_2$-$210_4$ and the computer connections $300_2$-$300_4$ with one of the interfaces $540_1$, $550_1$ and $560_1$ of the connection component $500_1$. The connection component $500_1$ is in turn connected via its communication interface $510_1$ and the computer connection $300_{n+i}$ with one of the interfaces $110_1$-$110_n$ of the computer 100. For example, only the connection component $500_1$ is thus directly connected with the computer 100. This can on the one hand lead to an unloading of the computer 100 and a reduction of the latency given transfers within the group of components $200_2$-$200_4$, and on the other hand to an increase of the latency given transfers between a component $200_2$-$200_4$ of the group and a component $200_1$, $200_n$ outside of the group, as well as a loss of the availability of all information in the computer 100.

Through the use of multiple (for example two, three, four or five) connection components, different topologies can be realized, for example hierarchies (such as recursive hierarchies), networks and layers. For example, a control device can furthermore comprise an additional connection component with communication interfaces that is logically arranged between the computer 100 and the connection component $500_1$; wherein the communication interface $510_1$ of the connection component $500_1$ is connected via a connection with a communication interface of the additional connection component; and an additional communication interface of the additional connection component is connected via the connection $300_{n+1}$ with one of the interfaces $110_1$-$110_n$ of the computer 100. Alternatively, a control device can furthermore comprise an additional connection component with communication interfaces that is logically arranged in parallel with the connection component $500_1$; wherein the communication interfaces of the components of an additional group are respectively connected via the connections with one of the interfaces of the additional connection component; and the communication interface of the additional connection component is connected via an additional connection with one of the interfaces $110_1$-$110_n$ of the computer 100.

Although modifications and changes may be suggested by those skilled in the art, it is the intention of the inventor to embody within the patent warranted hereon all changes and modifications as reasonably and properly come within the scope of his contribution to the art.

I claim as my invention:

1. A control assembly for an imaging system, said imaging system comprising a plurality of imaging system components, said control assembly comprising:
    a computer comprising a plurality n of computer communication interfaces, said computer being configured for centralized control of said imaging system components;
    each of said imaging system components comprising a component communication interface, with the respective component communication interfaces for all of said imaging system components being a total of n component communication interfaces;
    a plurality n of communication connections each proceeding only between one computer communication interface and one component communication interface;
    at least one of said imaging system components being configured as a transmitting component and at least one other of said imaging system components being configured as a receiving component, with the respective component communication interfaces of said transmitting component and said receiving component being configured to transmit information in an information transfer from said transmitting component to said receiving component exclusively via a communication path formed by the communication connection between the component communication interface of the transmitting component and the one computer connection interface connected thereto, said computer, and the communication connection between the component communication interface of the receiving component and said one computer communication interface connected thereto;
    a group controller connected to one of said computer communication interfaces and connected to multiple, but not all, imaging system components, with the respective component communication interfaces of said multiple imaging system components being connected, via respective ones of said communication connections and via said group controller, to said one computer communication interface to which said group controller is connected; and
    said group controller being configured to provide control information from said computer to said multiple imaging system components to control said multiple imaging system components as a group.

2. A control assembly as claimed in claim 1 wherein said receiving component is configured to request said information by transmitting a request to said computer via said communication path, and wherein said computer is configured to transmit said request to the transmitting component via said communication path.

3. A control assembly as claimed in claim 1 wherein said transmitting component is configured to transmit said information at a data rate and wherein said receiving component is configured to receive said information at said data rate, and wherein the respective component communication interfaces of said transmitting component and said receiving component are adapted to said data rate.

4. A control assembly as claimed in claim 1 wherein said plurality of communication connections are selected from the group consisting of hardwired connections and wireless connections.

* * * * *